United States Patent [19]
Chang et al.

[11] Patent Number: 5,990,365
[45] Date of Patent: *Nov. 23, 1999

[54] CATALYST COMPRISING ZSM-5, RHENIUM AND A SELECTIVATING AGENT

[75] Inventors: Clarence D. Chang, Princeton; Frank T. DiGuiseppi, Yardville; Scott Han, Lawrenceville, all of N.J.

[73] Assignee: Mobil Oil Corporation, Fairfax, Va.

[ * ] Notice: This patent issued on a continued prosecution application filed under 37 CFR 1.53(d), and is subject to the twenty year patent term provisions of 35 U.S.C. 154(a)(2).

[21] Appl. No.: 08/794,176

[22] Filed: Feb. 3, 1997

Related U.S. Application Data

[62] Division of application No. 08/352,646, Dec. 9, 1994, abandoned.

[51] Int. Cl.$^6$ ...................................................... C07C 5/22
[52] U.S. Cl. ................. 585/475; 585/470; 502/63; 502/64; 502/71; 502/85
[58] Field of Search ...................... 585/475, 470; 502/63, 64, 71, 77, 85

[56] References Cited

U.S. PATENT DOCUMENTS

| | | | |
|---|---|---|---|
| 4,275,256 | 6/1981 | Chu et al. | 585/467 |
| 5,321,183 | 6/1994 | Chang et al. | 585/475 |
| 5,349,113 | 9/1994 | Chang et al. | 585/475 |

*Primary Examiner*—Thomas Dunn
*Attorney, Agent, or Firm*—Peter W. Roberts; Malcolm D. Keen

[57] ABSTRACT

There is provided a catalyst comprising ZSM-5, rhenium which is impregnated onto the catalyst, and a selectivating agent. The selectivating agent may be coke and/or a siliceous material. The catalyst is particularly useful for catalyzing toluene disproportionation reactions. Methods for making this catalyst and processes for using this catalyst in toluene disproportionation are also provided.

16 Claims, No Drawings

CATALYST COMPRISING ZSM-5, RHENIUM AND A SELECTIVATING AGENT

This is a division of application Ser. No. 08/352,646, filed on Dec. 9, 1994, now abandoned.

BACKGROUND

There is provided a catalyst comprising ZSM-5, rhenium which is impregnated onto the catalyst, and a selectivating agent. The selectivating agent may be coke and/or a siliceous material. The catalyst is particularly useful for catalyzing toluene disproportionation reactions.

Shape-selective catalysis is described, e.g., by N. Y. Chen, W. E. Garwood, and F. G. Dwyer, *Shape Selective Catalysis in Industrial Applications*, 36, Marcel Dekker, Inc. (1989). Within a zeolite pore, hydrocarbon conversion reactions such as isomerization, disproportionation, alkylation, and transalkylation of aromatics are governed by constraints imposed by the channel size. Reactant selectivity may occur when a fraction of the feedstock is too large to enter the zeolite pores to react, while product selectivity may occur when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape-selective catalysis is demonstrated, for example, in selective alkyl-substituted benzene disproportionation to para-dialkyl-substituted benzene.

A representative para-dialkyl-substituted benzene is para-xylene. The production of para-xylene may be performed by methylation of toluene or by toluene disproportionation over a catalyst under conversion conditions. Examples include the reaction of toluene with methanol, as described by Chen et al., *J. Amer. Chem. Soc.*, 101, 6783 (1979), and toluene disproportionation, as described by Pines in *The Chemistry of Catalytic Hydrocarbon Conversions*, Academic Press, 72 (1981). Such methods may result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

The equilibrium reaction for the conversion of toluene to xylene and benzene proceeds as follows:

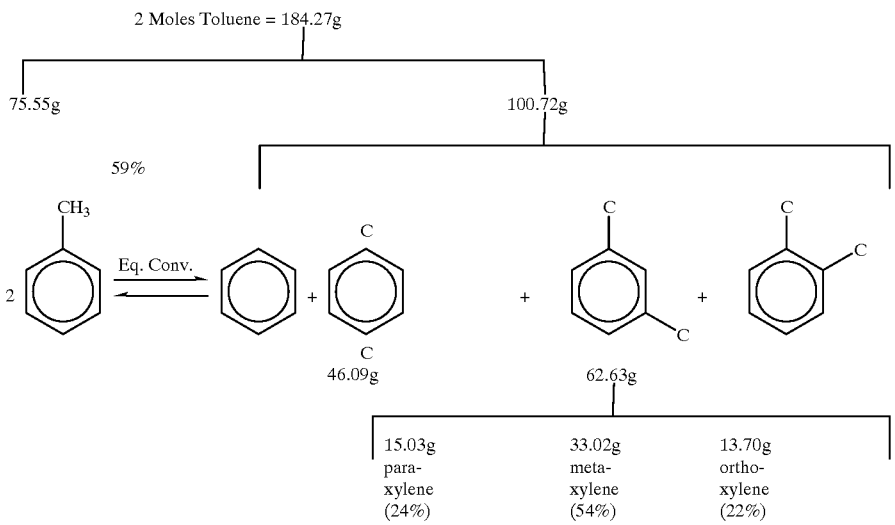

$$\text{p-Xylene Yield} = 100 \times \frac{15.03}{184.27} = 8.2\%$$

$$\text{p-Xylene Selectivity} = 100 \times \frac{15.03}{62.63} = 24\%$$

Various methods are known in the art for increasing the para-selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

Traditionally, ex situ pre-selectivation of zeolites has involved single applications of the modifying compound. It may be noted, however, that the suggestion of multiple treatments was made in U.S. Pat. No. 4,283,306 to Herkes. The Herkes patent discloses the promotion of crystalline silica catalyst by application of an amorphous silica such as ethylorthosilicate (i.e., tetraethylorthosilicate). The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that the multiple ex situ selectivation confers no benefit and in fact reduces a catalyst's efficacy in shape-selective reactions.

Steaming has also been used in the preparation of zeolite catalysts to modify the alpha or improve stability. For example, U.S. Pat. No. 4,559,314 describes steaming a zeolite/binder composite at 200–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

Various organic compounds have been employed as carriers for silicon compounds in the silicon impregnation methods applied to zeolite catalysts. For example, U.S. Pat. Nos. 4,145,315; 4,127,616; 4,090,981; and 4,060,568 describe the use of inter alia $C_{5-7}$ alkanes as solvents for silicon impregnation.

Noble metals, such as platinum, have been incorporated into catalysts for toluene disproportionation reactions for the purpose of reducing the generation of the unwanted by-product, ethylbenzene.

SUMMARY

There is provided a catalyst comprising ZSM-5, rhenium which is impregnated onto the catalyst, and at least one selectivating agent selected from the group consisting of coke and a siliceous material.

There is also provided a method for preparing a catalyst comprising combining ZSM-5 with rhenium, and at least one selectivating agent selected from the group consisting of coke and a siliceous material, wherein said rhenium is impregnated onto said catalyst.

There is also provided a process for disproportionating toluene, said process comprising contacting a feedstock with a catalyst under sufficient disproportionation conditions, said feedstock comprising toluene and hydrogen, and said catalyst comprising ZSM-5, rhenium which is impregnated onto the catalyst, and at least one selectivating agent selected from the group consisting of coke and a siliceous material.

EMBODIMENTS

In accordance with inventive subject matter described herein, it has been discovered that rhenium impregnation of a disproportionation catalyst comprising ZSM-5 reduces byproduct ethylbenzene (EB) during a toluene disproportionation process. Such reactions are usually run to maximize production of para xylene and byproduct EB contributes to the cost of separation. ZSM-5 catalysts containing rhenium have been discovered to reduce EB in selective disproportionation processes while showing low activity for undesired aromatics saturation. In addition, unlike noble metals, such as Pt and Pd, rhenium introduced onto ZSM-5 catalysts shows compatibility and maintain stability with selectivation procedures involving high temperature calcination treatments, which may be used to enhance para xylene selectivity. More particularly, for example, noble metals, such as platinum tend to agglomerate during the course of such high temperature calcination, thereby resulting in a reduced surface area and reduced catalytic effectiveness of the noble metal. Rhenium does not suffer from this deficiency to the degree of noble metals.

Data provided in Examples recited herein show that a ZSM-5 catalyst impregnated with rhenium, either before or after silicone selectivation, reduces EB and, in the case of impregnation before silicone treatment, maintains EB reduction activity even after multiple calcinations.

ZSM-5 may be selectivated with a siliceous material by a vapor phase process or a liquid phase process. An example of such a vapor phase process is described herein as a trim selectivation or in situ selectivation process. An example of a liquid phase selectivation process is described herein as a preselectivation or ex situ selectivation process. The trim selectivation treatment involves depositing siliceous material on the catalyst by contacting the catalyst with toluene, hydrogen and an organosilicon compound under toluene disproportionation conditions. The preselectivation treatment involves depositing siliceous material on the catalyst by the steps of:

(a) combining ZSM-5 with an organosilicon compound; and (b) calcining the organosilicon containing material in an oxygen containing atmosphere under conditions sufficient to remove organic material therefrom and leave the siliceous material on the ZSM-5.

Examples of trim selectivation techniques are provided in copending U.S. application Ser. No. 08/223,383, filed Apr. 5, 1994, now U.S. Pat. No. 5,498,814 as well as in copending U.S. application Ser. No. 08/233,542, filed May 5, 1994 now U.S. Pat. No. 5,495,179. Examples of preselectivation techniques are provided in copending U.S. application Ser. Nos. 08/069,251, now U.S. Pat. No. 5,476,823; 08/069,254, now U.S. Pat. No. 5,367,099; 08/069,255, now U.S. Pat. No. 5,403,800; and 08/069,259, now U.S. Pat. No. 5,365,004 each filed May 28, 1993.

The trim selectivation or the preselectivation treatment may result in the deposition of at least 1 wt % of siliceous material on the catalyst.

ZSM-5 may be combined with a binder material for the ZSM-5. This binder material is preferably an inert, non-alumina binder material, such as a silica binder. ZSM-5 may be subjected to one or more selectivation treatments and/or rhenium impregnations after the ZSM-5 is combined with the binder material. Optionally, however, the ZSM-5 may be selectivated and/or impregnated in the unbound state.

Procedures for preparing silica bound zeolites, such as ZSM-5, are described in U.S. Pat. Nos. 4,582,815; 5,053,374; and 5,182,242. A particular procedure for binding ZSM-5 with a silica binder involves an extrusion process.

A particular process for preparing silica bound ZSM-5 may comprise the steps of:

(a) mulling and then extruding a mixture comprising water, ZSM-5, colloidal silica and sodium ions under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said ZSM-5 with ammonium cations; and (c) calcining the ammonium exchanged extrudate of step (b) under conditions sufficient to generate the hydrogen form of said ZSM-5 and increase the crush strength of said extrudate.

The organosilicon compound which is used to trim selectivate the ZSM-5 may be a silicone or a silane. Silicones are defined herein as those compounds wherein silicon atoms are bonded to one another via oxygen atoms. Silanes are defined herein as those compounds wherein silicon atoms are bonded directly to one another.

The silicone compound which may be used to trim selectivate the ZSM-5 may be considered to be constructed of a siloxy backbone structure capped with terminal groups. This siloxy backbone structure may be a chain structure represented by the formula

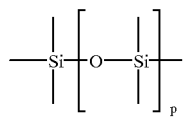

where p is from 1 to 9. This siloxy backbone structure may also be a cyclic structure represented by the formula

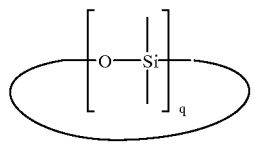

where q is from 2 to 10. Branched chain structures and composite chain/cyclic structures are also possible for the siloxy backbone of the silicone selectivating agent.

The hydrocarbyl groups which cap the available bonds of the siloxy backbone may have from 1 to 10 carbon atoms. Examples of such hydrocarbyl groups are methyl and phenyl.

Examples of silicone compounds having a chain siloxy backbone structure include those of the formula

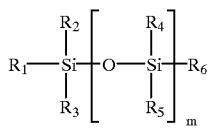

where $R_1$ and $R_6$ are independently hydrogen, methyl, or phenyl; $R_2$, $R_3$, $R_4$, and $R_5$ are independently methyl or phenyl; and m is from 1 to 10, e.g., from 1 to 4. Preferably, no more than one phenyl group is bonded to each silicon atom. Particular examples of such silicone compounds having a chain siloxy backbone structure include hexamethyldisiloxane, decamethyltetrasiloxane and diphenyltetramethyldisiloxane. Particular examples of silicone compounds having a cyclic siloxy backbone structure include octamethylcyclotetrasiloxane and decamethylcyclopentasiloxane. Particular examples of silicone compounds having a branched siloxy backbone structure are tris-(trimethylsiloxy)-phenylsilane and tris-(trimethylsiloxy)-silane.

The silane compounds, useful as trim selectivating agents, may have structures corresponding to the above-mentioned silicone compounds, wherein the silicon atoms are bonded directly to one another instead of via oxygen atoms. Examples of silanes having a chain backbone structure include those of the formula

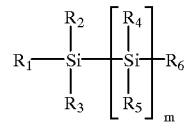

where $R_1$ and $R_6$ are independently hydrogen, methyl, or phenyl; $R_2$, $R_3$, $R_4$, and $R_5$ are independently methyl or phenyl; and m is from 1 to 10, e.g., from 1 to 4. An example of such a silane compound is hexamethyldisilane.

The present trim selectivation treatment is believed to result in the generation of functionalized zeolites, thereby serving to selectivate the zeolite for catalyzing certain reactions such as the disproportionation of toluene. Accordingly, the present trim selectivation treatment is also referred to herein as a functionalization treatment.

The ZSM-5 may be selectivated by more than one selectivation method, including those which are distinguished from selectivation methods described herein. In particular, prior to trim selectivation, the ZSM-5 may be preselectivated by contact with an organosilicon compound, followed by calcination in an oxygen containing atmosphere.

In accordance with examples of a preselectivation technique, the catalyst may be preselectivated by single or multiple treatments with a liquid organosilicon compound in a liquid carrier, each treatment being followed by calcination of the treated material in an oxygen containing atmosphere, e.g., air.

In accordance with the multiple impregnation preselectivation method, the ZSM-5 is treated at least twice, e.g., at least 3 times, e.g., from 4 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant.

Stable aqueous emulsions of organosilicon compounds (e.g., silicone oil) are described in copending U.S. application Ser. No. 08/141,758, filed Oct. 27, 1993, now abandoned. These emulsions are generated by mixing the organosilicon oil and an aqueous component in the presence of a surfactant or surfactant mixture. Useful surfactants include any of a large variety of surfactants, including ionic and non-ionic surfactants. Preferred surfactants include non-nitrogenous non-ionic surfactants such as alcohol, alkylphenol, and polyalkoxyalkanol derivatives, glycerol esters, polyoxyethylene esters, anhydrosorbitol esters, ethoxylated anhydrosorbitol esters, natural fats, oils, waxes and ethoxylated esters thereof, glycol esters, polyalkylene oxide block co-polymer surfactants, poly(oxyethylene-co-oxypropylene) non-ionic surfactants, and mixtures thereof. More preferred surfactants include surfactants having the formula α-[4-(1,1,3,3-tetramethylbutyl)phenyl]-ω-hydroxypoly(oxy-1,2-ethanediyl) (Octoxynols), most preferably octoxynol-9. Such preferred surfactants include the TRITON® X series, such as TRITON® X-100 and TRITON® X-305, available from Rohm & Haas Co., Philadelphia, Pa., and the Igepal CA series from GAF Corp., New York, N.Y. Emulsions formulated using such surfactants are effective for selectivating ZSM-5 to enhance shape selectivity, and to passivate surface acidity detrimental to product selectivity in certain regioselective catalytic applications such as the disproportionation of alkylbenzenes.

The organosilicon compound preselectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl-silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferred organosilicon preselectivating agents, particularly when the preselectivating agent is dissolved in an organic carrier or emulsified in an aqueous carrier, include dimethylphenylmethyl polysiloxane (e.g., Dow-550) and phenylmethyl polysiloxane (e.g., Dow-710). Dow-550 and Dow-710 are available from Dow Chemical Co., Midland, Mich.

When the organosilicon preselectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as —$N(CH_3)_3$, —$N(C_2H_5)_3$ and —$N(C_3H_7)_3$. A preferred water soluble organosilicon preselectivating agent is an n-propylamine silane, available as Hydrosil 2627 from Huls America.

When the ZSM-5 is preselectivated by a single or multiple impregnation technique, the ZSM-5 is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof. However, this siliceous solid residue material may also comprise carbon atoms in the structure thereof, resulting from the residue of the organo portion of the organosilicon compound used to impregnate the catalyst.

Following each impregnation, the zeolite may be calcined at a rate of from about 0.2° C./minute to about 5° C./minute to a temperature greater than 200° C., but below the temperature at which the crystallinity of the zeolite is adversely affected. This calcination temperature may be below 600° C., e.g., within the approximate range of 350° C. to 550° C. The duration of calcination at the calcination temperature may be from 1 to 24 hours, e.g., from 2 to 6 hours.

The impregnated zeolite may be calcined in an inert or oxidizing atmosphere. An example of such an inert atmosphere is a nitrogen, i.e., $N_2$, atmosphere. An example of an oxidizing atmosphere is an oxygen containing atmosphere, such as air. Calcination may take place initially in an inert, e.g., $N_2$, atmosphere, followed by calcination in an oxygen containing atmosphere, such as air or a mixture of air and $N_2$. Calcination should be performed in an atmosphere substantially free of water vapor to avoid undesirable uncontrolled steaming of the zeolite. The zeolite may be calcined once or more than once following each impregnation. The various calcinations following each impregnation need not be identical, but may vary with respect to the temperature, the rate of temperature rise, the atmosphere and the duration of calcination.

The amount of siliceous residue material which is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and duration of the calcination.

Preferably, the kinetic diameter of both the organosilicon compound, which is used to preselectivate the zeolite, and the organosilicon compound (e.g., silicone compound), which is used to functionalize the zeolite, is larger than the zeolite pore diameter, in order to avoid entry of the organosilicon compound into the zeolite pores and any concomitant reduction in the internal activity of the zeolite.

In accordance with the trim selectivation or functionalization method described herein, the zeolite is contacted with a feed stream comprising a silicone or silane compound under vapor phase conditions. The silicone or silane compound may be applied to the zeolite neat (i.e., in the absence of a carrier or other cofeed) by a chemical vapor deposition technique. This feed stream may also comprise hydrogen and/or an organic carrier. Vapor phase conditions may include a temperature ranging from about 100° C. to about 600° C., e.g., from about 300° C. to about 500° C. When the silicone or silane compound is applied neat, reduced pressures, e.g., from about 0.5 Torr to less than atmospheric, may be used. Preferably, however, the silicone or silane compound is applied along with cofed hydrogen (i.e., $H_2$) and an organic carrier. In general, vapor phase conditions may include a pressure ranging from about 0 to about 2000 psig, e.g., from about 15 to about 800 psig, a mole ratio of hydrogen to hydrocarbons (e.g., toluene) from about 0.1 to 20, e.g., from about 0.1 to 10, e.g., from about 1 to about 4, and a weight hourly space velocity (WHSV) from about 0.1 to about 100 $hr^{-1}$, e.g., from about 0.1 to about 10 $hr^{-1}$. The organic carrier may be a hydrocarbon, especially an aromatic hydrocarbon such as toluene, benzene, xylenes and trimethylbenzenes. Toluene may comprise about 50 wt % to 100 wt %, e.g., at least 80 wt %, of the hydrocarbons in the feedstock.

When a reactive hydrocarbon, such as toluene is included in the feedstock, the presence of a sufficient amount of hydrogen in the selectivation feedstock is necessary to prevent rapid aging of the catalyst during the selectivation process resulting in an excessive reduction in the zeolite activity, possibly accompanied by a reduction in toluene disproportionation selectivity to para-xylene. This rapid aging is believed to result from a rapid build-up of excessive amounts of carbonaceous deposits (i.e., coke), which may even extend into the pore system of the zeolite in the catalyst. However, even when hydrogen is used in optimal fashion to prevent aging during the selectivation process, a small amount of carbonaceous deposit may form on the catalyst. The presence of hydrogen may also serve to induce or enhance the chemical reaction between the zeolite and the selectivating agent, which results in the functionalization of the zeolite. This chemical reaction is also believed to be induced or enhanced by elevated contact temperatures, which may be needed to maintain the silicone or silane functionalizing agent in the vapor phase.

Confirmation of the reaction between the zeolite and the silicone or silane compound may be made by an appropriate analysis of the zeolite after the reaction, as well as by monitoring and analyzing the off-gases produced by the reaction. Analysis of the zeolite will indicate the presence of hydrocarbyl groups incorporated onto the zeolite from the organosilicon selectivating agent. When the functionalized zeolite is used as a catalyst in an organic conversion process, these hydrocarbyl groups may remain intact on the zeolite. More particularly, it is preferred to intentionally avoid the customary practice of precalcining the zeolite, prior to the organic conversion process, under conditions sufficient to decompose and/or burn off organic residue on the catalyst. Such precalcination conditions to be avoided may include contact of the zeolite at temperatures greater than 300° C. in an oxygen-containing atmosphere, e.g., air.

As pointed out in U.S. Pat. No. 4,117,026, the para-selectivity of certain catalysts adapted for the disproportionation of toluene may be improved by controlled coking of the catalyst. The present catalyst may also be subjected to controlled coking. This controlled coking procedure is also referred to herein as coke selectivation. This optional coke selectivation may involve contacting the catalyst with a thermally decomposable organic compound at an elevated temperature of said compound but below the temperature at which the crystallinity of the zeolite is adversely affected. This contact temperature may be, for example, less than about 650° C.

Organic materials, which may be used for this coke selectivation process, encompass a wide variety of compounds including by way of example, hydrocarbons, such as paraffinic, cycloparaffinic, olefinic, cycloolefinic and aromatic; oxygen-containing organic compounds, such as alcohols, aldehydes, ethers, ketones and phenols; and heterocyclics, such as furans, thiophenes, pyrroles and pyridines. A hydrogen cofeed may be used to deter the excessive build-up of coke. Further details regarding coke selectivation techniques are provided in the aforementioned U.S. Pat. No. 4,117,026, as well as in copending U.S. application Ser. No. 08/069,251, filed May 28, 1993, now U.S. Pat. No. 5,476,823. An organosilicon cofeed may be, optionally, included along with the organic material feed used for coke selectivation. This organosilicon material may be selected from the organosilicon compounds mentioned hereinabove for use in the trim-selectivation of the catalyst.

The coke selectivation treatment of the catalyst may result in the deposition of at least 2 wt. % of coke on the catalyst.

The presently modified ZSM-5 is a catalyst. This catalyst may be used alone or in combination with other catalyst components included in catalysts of this type. Such other components include binders and hydrogenation/dehydrogenation components. Accordingly, it will be understood that the term, present catalyst, as used herein is intended to connote the presently modified zeolite in combination with other catalyst components, if any.

The present zeolite may optionally be treated, before, during or after contact with the organosilicone or coke selectivating agent, with selectivating agents containing atoms other than silicon or carbon. Such optional selectivation agents may include atoms such as P, Mg, B, N, Ce, Ca and Sr. However, insofar as the present catalyst may be free of treatment with such optional selectivation agents, the present catalyst may contain less than 500 ppm of each of the following elements as measured by elemental analysis: P, Mg, B, N, Ce, Ca, and Sr.

While not wishing to be bound by any theory, it is theorized that the extreme selectivity of the present catalyst is obtained by rendering acid sites on the external surfaces of the zeolite substantially inaccessible to reactants, while possibly increasing the tortuosity of the catalyst pore system. In a toluene disproportionation process using a non-selectivated catalyst, acid sites existing on the external surfaces of the zeolite are believed to isomerize the product para-xylene back to an equilibrium level with the other two xylene isomers, thereby reducing the amount of para-xylene in the xylenes to only about 24%. By reducing the availability of these external acid sites to the product para-xylene, it is theorized that a relatively high proportion of the para isomer can be retained. It is theorized that external zeolite acid sites are blocked or otherwise unavailable to para-xylene in the present catalyst. The extreme para-selectivity of the present catalyst is especially surprising in the highly active forms of the catalyst.

The "alpha value" of a catalyst is an approximate indication of its catalytic cracking activity. The alpha test is described in U.S. Pat. No. 3,354,078 and in the *Journal of Catalysis*, Vol. 4, 522–529 (1965); Vol. 6, 278 (1966); and Vol. 61, 395 (1980), each incorporated herein by reference to that description. It is noted that intrinsic rate constants for many acid-catalyzed reactions are proportional to the alpha value for a particular crystalline silicate catalyst (see "The Active Site of Acidic Aluminosilicate Catalysts," *Nature*, Vol. 309, No. 5959, 589–591, (1984). The experimental conditions of the alpha test preferably include a constant temperature of 538° C. and a variable flow rate as described in detail in the *Journal of Catalysis*, Vol. 61, 395 (1980). The present catalysts may have an alpha value greater than 50, e.g., greater than 200, e.g., from about 200 to about 500. The alpha value of the catalyst may be increased by initially treating the catalyst with organic or mineral acid, e.g., oxalic acid or nitric acid, or by mild steaming before selectivation. This type of steaming is discussed in U.S. Pat. No. 4,326,994.

The silica to alumina ratio of zeolites may be determined by conventional analysis. This ratio is meant to represent, as closely as possible, the ratio in the rigid atomic framework of the zeolite crystal and to exclude silicon or aluminum in the binder or in cationic or other form within the channels. The silica to alumina molar ratio of the ZSM-5 used to prepare the present catalysts may be less than 60, e.g., less than 40, e.g., from about 20 to about 40. It will be appreciated that it may be extremely difficult to directly measure the silica to alumina ratio of zeolite after it has been combined with a binder material and selectivated by methods described hereinabove. Accordingly, the silica to alumina ratio has been expressed hereinabove in term of the silica to alumina ratio of the parent zeolite, i.e., the zeolite used to prepare the catalyst, as measured prior to the selectivation of the zeolite and prior to the combination of this zeolite with the other catalyst components.

The crystal size of the parent zeolites of the present catalysts is preferably greater than 0.1 microns, as calculated by methods described hereinbelow. The accurate direct measurement of the crystal size of zeolite materials is frequently very difficult. Microscopy methods, such as SEM and TEM, may be used, but these methods require measurements of a large number of crystals and, for each crystal measured, values may be evaluated in up to three dimensions. Furthermore, in order to more completely characterize the crystal size of a batch of crystals, one should calculate the average crystal size, as well as the degree of variance from this average in terms of a crystal size distribution. Rather than relying upon such complex evaluations, crystal size is expressed herein in terms of a calculated value of average crystal size obtained by measuring the rate of sorption of 2,2-dimethylbutane at 90° C. and 60 torr hydrocarbon pressure. The crystal size is computed by applying the diffusion equation given by J. Crank, *The Mathematics of Diffusion,* Clarendon Press, 52–56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{0.3}$, the time required for the uptake of 30% capacity of hydrocarbon, is:

$$d = 0.0704 \times t_{0.3}^{1/2}.$$

Particular measurements expressed herein were made on a computer controlled, thermogravimetric electrobalance, but there are numerous ways one skilled in the art could obtain the data. Examples of larger crystal material described herein have a sorption time, $t_{0.3}$, of 497 minutes, which gives a calculated crystal size of 1.6 microns. Examples of smaller crystal material described herein have a sorption time of 7.8 minutes, and a calculated size of 0.20 microns.

As pointed out in the aforementioned U.S. Pat. No. 4,117,026, larger crystal size zeolites tend to have a greater intrinsic para-selectivity than smaller crystal size zeolites. It is theorized that this difference is attributable to the smaller ratio of external surface area to available internal surface area for larger zeolites as compared to smaller crystal size zeolites. Since it would theoretically require less selectivation to neutralize the external surface area of the more intrinsically para-selective larger crystal size zeolites, larger crystal size zeolites would be preferred to smaller crystal size zeolites, provided that all other factors were equal. However, there are other factors which tend to mitigate against a preference for larger crystal size zeolites, particularly ZSM-5. More particularly, larger crystal size ZSM-5 having a high activity and corresponding low silica to alumina molar ratio, e.g., from about 20 to about 40, is considerably more difficult to prepare than smaller crystal size ZSM-5, especially on a commercial scale. A particularly surprising aspect of the present siliceous material selectivated catalysts is that the zeolites thereof may comprise relatively small crystal size ZSM-5, e.g., having a crystal size of from about 0.1 to about 0.5 microns and a silica to alumina molar ratio of from about 20 to 40, and still have an extremely high degree of para-selectivity. When larger crystal size ZSM-5 is chosen for the present catalyst, the crystal size of this ZSM-5 may be, for example, from about 1 to 2 microns.

Impregnation with rhenium (Re) may take place by contacting the catalyst with a solution, preferably an aqueous solution, of at least one rhenium compound, whereby the solution is sorbed onto the surface and the accessible internal pore structure of the catalyst. Thereafter, the catalyst is dried under conditions to leave a residue of the rhenium compound in the catalyst. After drying, the catalyst may be calcined under conditions to generate an oxide form of rhenium.

The impregnation treatment need not result in the ion exchange of any cations in the ZSM-5 with rhenium cations. More particularly, for example, the rhenium compound used to impregnate the catalyst may include the rhenium element in the anionic portion thereof. A particular example of such a rhenium compound is $NH_4ReO_4$.

When the catalyst, which is impregnated, comprises a binder material, the rhenium element, which is impregnated onto the catalyst, can be but need not be in direct physical contact with the ZSM-5 in the catalyst. This rhenium may be located in the binder portion of the catalyst, closely associated with the ZSM-5. The rhenium impregnation may be repeated one or more times.

The amount of rhenium, which is impregnated onto the catalyst, may be at least 0.01 wt. %, e.g., from about 0.05 wt. % to about 5 wt. %.

The present catalyst is particularly adapted for the production of para-xylene via the catalytic disproportionation of toluene. More particularly, this catalyst, under disproportionation conditions, is capable of high conversions of toluene, while at the same time producing a very high proportion of para-xylene among the total of the xylene isomers. However, it will be understood that this catalyst may also be used to catalyze other organic, especially hydrocarbon, conversion reactions.

When the present catalyst is used in a toluene disproportionation reaction, the reaction conditions may include a temperature of about 350° C.–540° C., a pressure of about atmospheric—5000 psig, a toluene feed rate of about 0.1–20 WHSV, and a hydrogen to toluene mole ratio of about 0.1–20. The hydrogen cofeed serves to suppress catalyst aging, thereby dramatically increasing the cycle length.

When the present catalyst is used in an ethylbenzene disproportionation reaction, the reaction conditions may include a temperature of about 200° C. to about 600° C., e.g., from about 350° C. to about 540° C.; a pressure of from about atmospheric to about 5000 psig, e.g., from about 100 to about 1000 psig; an ethylbenzene feed rate of from about 0.1 WHSV to about 20 WHSV, e.g., from about 2 WHSV to about 10 WHSV; and a hydrogen to ethylbenzene mole ratio of from about 0.1 to about 20, e.g., from about 2 to about 6.

The present catalysts may be used to convert paraffins from high to low molecular weight hydrocarbons in a dewaxing process. Examples of such dewaxing processes are disclosed in U.S. Pat. Nos. 3,700,585; Re. 28,398; 3,968,024; and 4,181,598, the entire disclosures of which are incorporated herein by reference. Hydrocarbon feeds for dewaxing processes include petroleum stocks which have a freeze point or pour point problem, e.g., petroleum stocks boiling above 350° F. Lubricating oil stocks may be feedstocks to a dewaxing process. The dewaxing may be carried out under either cracking or hydrocracking conditions. Cracking conditions for dewaxing may include a liquid hourly space velocity (LHSV) between about 0.5 and 200, a temperature between about 288° C. (550° F.) and 590° C. (1100° F.), a pressure between about subatmospheric and several hundred atmospheres. Hydrocracking conditions for dewaxing may include a liquid hourly space velocity (LHSV) between about 0.1 and 10, a temperature between about 340° C. (650° F.) and 538° C. (100° F.), a pressure between about 100 and 3000 psig, and a hydrogen to hydrocarbon mole ratio between about one and 20.

The present catalysts may be used to catalyze a variety of alkylaromatic conversion reactions, including isomerization reactions. Such conversions include those described, for example, in U.S. Pat. Nos. 3,856,872; 3,856,873; Re. 30,157; 4,101,595; 4,101,597; 4,312,790; Re. 31,919; and 4,224,141, the entire disclosures of which are incorporated by reference.

As per process conditions described in U.S. Pat. No. 3,856,872 to Morrison, the present catalyst may be used for catalyzing the conversion of $C_8$ aromatics, i.e., xylene and/or ethylbenzene, to para-xylene (octafining) at a temperature of 550° F. (288° C.) to 900° F. (482° C.), a pressure of 150 to 300 psig, and a liquid hourly space velocity (LHSV) of 1 to 200. When used in this reaction, the catalyst may comprise a hydrogenation metal, such as platinum or nickel, and the feed to the reaction may include hydrogen.

As per process conditions described in U.S. Pat. No. 3,856,873 to Burress, the present catalyst may be used for catalyzing the conversion of mixtures of $C_8$ aromatic hydrocarbons to para-xylene in a vapor phase reaction at a temperature of 500° F. (260° C.) to 1000° F. (538° C.), a pressure of 0 (atmospheric) to 1000 psig, and a weight hourly space velocity (WHSV) of 0.5 to 250 with no added hydrogen.

As per process conditions described in U.S. Pat. No. 4,476,330 to Kerr et al., the present catalyst may be used for catalyzing the conversion of aliphatic oxygenates to a higher molecular weight compound at a temperature of 70° F. (21° C.) to 1400° F. (760° C.). The feeds include lower aliphatic organic oxygenates having up to 6 carbon atoms. The oxygenates may be selected from the group consisting of acetals, ketals, acid halides, alcohols, carboxylic acids, aldehydes, acid anhydrides, epoxides, ethers, hemiacetals, gem diols, hydroxy acids, ketones, ketenes, lactones, peracids, peroxides and sugars, especially alcohols, ethers and esters.

The present catalysts may be used as catalysts in the oligomerization of olefins to form gasoline, distillate, lube oils and/or chemicals. Examples of such oligomerization processes are disclosed in U.S. Pat. Nos. 4,517,399; 4,520,221; 4,547,609; and 4,547,613, the entire disclosures of which are incorporated herein by reference.

As per process conditions described in U.S. Pat. No. 4,517,399 to Chester et al., the present catalyst may be used for catalyzing the conversion of olefins having from 3 to 18 carbon atoms, e.g., propylene, to high viscosity, low pour point lubricating oils. Conversion conditions may include a temperature of 350° F. (177° C.) to 650° F. (343° C.), a pressure of 100 to 5000 psig, and a weight hourly space velocity (WHSV) of 0.1 to 10.

The present catalysts may be used as catalysts in the conversion of a variety of aromatic compounds to provide dialkyl-benzene products which are highly enriched in the para-dialkyl substituted benzene isomer. Conversion reactions of this type include aromatics alkylation, transalkylation and disproportionation. Examples of such aromatic alkylation processes are disclosed in U.S. Pat. Nos. 3,755,483; 4,086,287; 4,117,024; and 4,117,026, the entire disclosures of which are incorporated herein by reference.

As per process conditions described in U.S. Pat. No. 3,755,483 to Burress, the present catalyst may be used for catalyzing the alkylation of aromatic hydrocarbons, such as benzene, naphthalene, anthracene and substituted derivatives thereof, e.g., toluene and xylene, with alkylating agents having 1 to 24 carbon atoms under vapor phase conditions. The alkylating agents may be selected from the group consisting of olefins, such as ethylene, propylene and dodecene, aldehydes, such as formaldehyde, alkyl halides and alcohols. Conversion conditions may include an inlet temperature of up to about 900° F. (428° C.), with a reactor bed temperature of up to about 1050° F. (566° C.), a pressure of about atmospheric to about 3000 psig, a ratio of aromatic/alkylating agent of about 1:1 to about 20:1 and a weight hourly space velocity (WHSV) of 20 to 3000.

As per process conditions described in U.S. Pat. No. 4,086,287 to Kaeding et al., the present catalyst may be used for catalyzing the ethylation of toluene or ethylbenzene to produce a para-ethyl derivative, e.g., para-ethyltoluene. Conversion conditions may include a temperature of from about 250° C. to about 600° C., a pressure of 0.1 atmospheres to about 100 atmospheres, a ratio of aromatic/ethylating agent of about 1:1 to about 10:1 and a weight hourly space velocity (WHSV) of 0.1 to 100.

The present catalysts may be used as catalysts in the conversion of light paraffins and olefins to aromatic compounds. Examples of such conversions are disclosed in U.S. Pat. Nos. 3,760,024 and 3,756,942, the entire disclosures of which are incorporated herein by reference.

As per process conditions described in U.S. Pat. No. 3,760,024 to Cattanach, the present catalyst may be used for catalyzing the conversion of paraffins having 2 to 4 carbon atoms and/or olefins to aromatics having from 6 to 10 carbon atoms. The catalyst may, optionally, include a hydrogenation/dehydrogenation component. Conversion conditions may include a temperature of from about 100° C. to about 650° C., a pressure of 0 to about 1000 psig, a ratio of hydrogen/hydrocarbon of about 0 to about 20 and a weight hourly space velocity (WHSV) of 0.1 to 500.

The present catalysts may be used as catalysts in the synthesis of pyridine and substituted pyridines. Process conditions may be selected from those disclosed in U.S. Pat. Nos. 4,675,410 and 4,220,783, the entire disclosures of which are incorporated herein by reference.

The present catalysts may be used as catalysts in the synthesis of caprolactam by the Beckmann rearrangement of cyclohexane oxime. Process conditions may be selected from those disclosed in U.S. Pat. No. 4,359,421, the entire disclosures of which are incorporated herein by reference.

Accordingly, it will be understood that the present catalysts may be used to catalyze a variety of organic, e.g., hydrocarbon, conversion processes. Examples of such processes include cracking hydrocarbons with reaction conditions including a temperature of from about 300° C. to about 700° C., a pressure of from about 0.1 atmosphere (bar) to about 30 atmospheres and a weight hourly space velocity of from about 0.1 $hr^{-1}$ to about 20 $hr^{-1}$; dehydrogenating hydrocarbon compounds with reaction conditions including a temperature of from about 300° C. to about 700° C., a pressure of from about 0.1 atmosphere to about 10 atmospheres and weight hourly space velocity of from about 0.1 to about 20; converting paraffins to aromatics with reaction conditions including a temperature of from about 300° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g., benzene, toluene and xylene, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g., methanol, or ethers, e.g., dimethylether, or mixtures thereof to hydrocarbons including olefins and/or aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure from about atmospheric to about 60 atmospheres and a weight hourly space velocity of from about 0.08 to about 20; alkylating aromatic hydrocarbons, e.g., benzene and alkylbenzenes in the presence of an alkylating agent, e.g., olefins, formaldehyde, alkyl halides and alcohols, with reaction conditions including a temperature of from about 250° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylkating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/ polyalkylaromatic hydrocarbon mole ratio of from about 1/1 to about 16/1.

In general, therefore, catalytic conversion conditions over the present catalyst may include a temperature of from about 100° C. to about 760° C., a pressure of from about 0.1 atmosphere (bar) to about 200 atmospheres (bar), a weight hourly space velocity of from about 0.08 hr$^{-1}$ to about 2000 hr$^{-1}$ and a hydrogen/organic, e.g., hydrocarbon compound, of from 0 to about 100.

Especially when the present catalyst is intended for use as a toluene disproportionation process, the binder for this catalyst is preferably an inert, non-alumina containing material, such as silica. However, the binder may also be selected from other materials which may be used exclusively or in combination with one another or with silica. Examples of such binder materials include alumina, zirconia, magnesia, titania, thoria and boria. These materials may be used in the form of dried inorganic oxide gels of gelatinous precipitates. Examples of clay binder materials include bentonite and kieselguhr. The relative proportion of zeolite to the binder material may be about 30 to about 90 percent by weight. The bound catalyst may be in the form of an extrudate, beads or fluidizable microspheres.

The rhenium component of the present catalyst is believed to perform a hydrogenation/dehydrogenation function. This rehenium component may be the sole hydrogenation/ dehydrogenation component of the present catalyst. Optionally, however, the present catalyst may contain other hydrogenation/dehydrogenation components in addition to the rhenium component. Examples of such optional components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi), and Group VIIB metals (i.e., Mn, Tc and Re). Noble metals (i.e., Pt, Pd, Ir, Rh, Os and Ru) are particular optional hydrogenation/ dehydrogenation components. Combinations of catalytic forms of such noble or non-noble metal, such as combinations of Pt with Sn, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction. Preferably, the present catalyst is free of noble metal.

The optional hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetrammineplatinum complexes, platinum chloride, tin sulfate and tin chloride.

The amount of optional hydrogenation/dehydrogenation component may be that amount which imparts or increases the catalytic ability of the overall catalyst to catalytically hydrogenate or dehydrogenate an organic compound under sufficient hydrogenation or dehydrogenation conditions. This amount is referred to herein as a catalytic amount. Quantitatively speaking, when the present catalyst comprises a noble metal, it may comprise, for example, from about 0.001 to about 5 wt %, e.g., from about 0.1 to about 2 wt %, of the noble metal.

The following Examples illustrate the present concepts. The catalyst used was a 65% HZSM-5 (SiO$_2$/Al$_2$O$_3$=26)/ 35% silica extrudate.

EXAMPLE 1

Surfactant Mixture

A 70/30 surfactant mixture was prepared by mixing 14.0 g of Triton X-100 and 6.0 g of Triton X-305 which became cloudy after sitting at room temperature.

EXAMPLE 2

Water/Surfactant Mixture

A water/surfactant stock solution used to emulsify Dow silicone oil was prepared by mixing 17.0 g of the 70/30 surfactant mixture in Example 1 with 983.0 g of distilled water. The resulting solution contained 1.7% surfactant in water.

EXAMPLE 3

Silicone Oil/Water Emulsion

An aqueous silicone oil/water emulsion was prepared by mixing 65.0 wt. % of DC-710 (DOW phenymethyl silicone oil) with 1.7 wt. % of the surfactant mixture in Example 1, the balance being distilled water. This solution was emulsified by mixing in a blender for 1 minute. This emulsion separated slightly upon sitting overnight. Mildly shaking the solution successfully restored the emulsion.

EXAMPLE 4

Base Case Catalyst 22.10 g of HZSM-5 catalyst was weighed out and dried at 120° C.. The catalyst was contacted with a mixture of solutions from Examples 2 and 3 above. The solvent was stripped in vacuum and dried at 120° C. The catalyst was then calcined at 538° C. in N$_2$ for 4 hours. This procedure was repeated 4 additional times (total 5 treatments). The weights used are below:

| Treatment Number | Emulsion | Surfactant |
|---|---|---|
| 1 | 5.11 g | 12.57 g |
| 2 | 5.11 g | 13.64 g |
| 3 | 5.11 g | 14.23 g |
| 4 | 9.06 g | 10.94 g |
| 5 | 5.76 g | 14.17 g |

EXAMPLE 5

Re/ZSM-5 Catalyst

The HZSM-5 catalyst was dried at 120° C. and 0.1 wt. % Re was impregnated using incipient wetness and $NH_4ReO_4$ starting reagent. The catalyst was then dried at 120° C. and selectivated 3 times using the procedure described in Example 4. The starting weight of Re/ZSM-5 was 2.42 g and the weights used are below:

| Treatment Number | Emulsion | Surfactant |
|---|---|---|
| 1 | 0.74 g | 1.77 g |
| 2 | 0.63 g | 1.40 g |
| 3 | 0.70 g | 1.75 g |

EXAMPLE 6

Re/ZSM-5 Catalyst

The HZSM-5 catalyst was dried at 120° C. and 0.25 wt. % Re was impregnated using incipient wetness and $NH_4ReO_4$ starting reagent. The catalyst was then dried at 120° C. and selectivated 3 times using the procedure described in Example 4. The starting weight of Re/ZSM-5 was 2.42 g and the weights used are below:

| Treatment Number | Emulsion | Surfactant |
|---|---|---|
| 1 | 0.56 g | 1.48 g |
| 2 | 0.56 g | 1.51 g |
| 3 | 0.70 g | 1.75 g |

EXAMPLE 7

Pt/ZSM-5 Catalyst

For comparison purposes, a Pt/ZSM-5 catalyst was prepared by ion-exchanging 0.1 wt. % Pt onto the HZSM-5 catalyst using $Pt(NH_3)_4Cl_2$. The resultant catalyst was calcined at 400° C. in $N_2$ for 3 hours. No silicone selectivations were performed.

EXAMPLE 8

Catalytic Testing

The catalysts from Examples 4–7 above were tested for toluene disproportionation. In all cases, 2.0 g of 20–40 mesh catalyst was charged to a 3/8" o.d. micro-reactor. Unit conditions were 300 psig, 3 WHSV, 2:1 $H_2$/HC, with temperatures sufficient to achieve ~30 wt. % toluene conversion. Feed toluene was purified by passing over activated alumina. Products were analyzed on-line by GC. Data are given in Table 1.

TABLE 1

Catalytic Toluene Disproportionation Testing at 300 psig, 3 WHSV, 2:1 $H_2$/HC for HZSM-5, Re/ZSM-5, Pt/ZSM-5

| | HZSM-5 | | 0.1% Re/ZSM-5 | | 0.25% Re/ZSM-5 | | Pt/ZSM-5 | |
|---|---|---|---|---|---|---|---|---|
| Example | 4 | 4 | 5 | 5 | 6 | 6 | 7 | 7 |
| Time on Stream, h | 72 | 73 | 63 | 95 | 113 | 190 | 13 | 19 |
| Temperature, ° C. | 440 | 440 | 466 | 468 | 446 | 468 | 380 | 380 |
| Product Dist., wt. % | | | | | | | | |
| $C_5^-$ | 2.2 | 2.4 | 2.3 | 2.6 | 2.3 | 2.3 | 1.9 | 3.0 |
| Benzene | 19.7 | 20.0 | 13.6 | 14.1 | 13.7 | 14.0 | 12.4 | 12.6 |
| Toluene | 69.4 | 68.4 | 71.2 | 70.0 | 70.3 | 70.0 | 66.6 | 66.2 |
| Ethylbenzene | 0.3 | 0.3 | 0.1 | 0.1 | 0.1 | 0.1 | 0.3 | 0.3 |
| p-Xylene | 5.6 | 5.9 | 8.9 | 9.1 | 9.4 | 9.5 | 4.3 | 4.2 |
| m-Xylene | 2.1 | 2.2 | 3.1 | 3.2 | 3.4 | 3.4 | 9.2 | 8.9 |
| o-Xylene | 0.4 | 0.4 | 0.5 | 0.5 | 0.5 | 0.5 | 3.9 | 3.6 |
| $C_9^+$ | 0.3 | 0.4 | 0.3 | 0.4 | 0.3 | 0.2 | 1.6 | 1.2 |
| Toluene conv., wt. % | 30.6 | 31.6 | 28.8 | 30.0 | 29.7 | 30.0 | 33.4 | 33.8 |
| p-Xylene sel., % | 69.1 | 69.4 | 71.2 | 71.1 | 70.7 | 70.9 | 24.7 | 25.1 |
| Ethylbenzene sel. of $C_8$'s, % | 3.6 | 3.4 | 0.8 | 0.8 | 0.7 | 0.7 | 1.7 | 1.8 |

The data show that Re/ZSM-5 is active for ethylbenzene (EB) reduction during toluene disproportionation. EB reductions of 75–80% over the base case catalyst were observed. Additionally, a Pt/ZSM-5 showed relatively poorer EB reduction activity versus Re/ZSM-5 even though that catalyst was subjected to less severe and fewer calcinations (1× at 400° C. for Pt/ZSM-5 versus 3× at 538° C. for Re/ZSM-5).

What is claimed is:

1. A selectivated catalyst comprising: ZSM-5, rhenium impregnated onto the catalyst in an amount of at least about 0.01 wt %, and at least one selectivating agent selected from the group consisting of coke and a siliceous material, wherein the catalyst is selectivated so as to provide at least about 70.7% reaction selectivity to para-xylene over other xylene isomers, and further wherein when said selectivating agent is coke, said coke is present in the catalyst in the amount of at least about 2 wt %, and when said selectivating agent is a siliceous material, said siliceous material is present in an amount of at least about 1 wt %.

2. A catalyst according to claim 1, wherein said ZSM-5 has a silica to alumina molar ratio of 60 or less.

3. A catalyst according to claim 1, wherein said coke is deposited on said catalyst by contacting said catalyst with toluene and hydrogen under toluene disproportionation conditions.

4. A catalyst according to claim 1, wherein said siliceous material is deposited on said catalyst by contacting said catalyst with toluene, hydrogen and an organosilicon compound under toluene disproportionation conditions.

5. A catalyst according to claim 1, further comprising a binder material.

6. A catalyst according to claim 5, wherein said binder material is silica.

7. A catalyst according to claim 1, wherein said siliceous material is deposited on said catalyst by the steps of
   (a) combining a bound form of ZSM-5 with an organosilicon compound; and
   (b) calcining the organosilicon containing material in an oxygen containing atmosphere under conditions sufficient to remove organic material therefrom and leave said siliceous material on the bound ZSM-5.

8. A catalyst according to claim 7, wherein steps (a) and (b) are repeated at least once.

9. A method for preparing a selectivated catalyst comprising:
   combining ZSM-5 with rhenium and at least one selectivating agent selected from the group consisting of coke and a siliceous material, wherein said rhenium is impregnated onto said catalyst in an amount of at least about 0.01 wt %, and wherein the catalyst is selectivated so as to provide at least about 70.7% reaction selectivity to para-xylene over other xylene isomers, and further wherein when said selectivating agent is coke, said coke is present in the catalyst in the amount of at least about 2 wt %, and when said selectivating agent is a siliceous material, said siliceous material is present in an amount of at least about 1 wt %.

10. A method according to claim 9, wherein said selectivating agent is added to the catalyst after rhenium is added to the catalyst.

11. A method according to claim 9, wherein said selectivating agent is added to the catalyst before rhenium is added to the catalyst.

12. A method according to claim 9, wherein coke is deposited on said catalyst by contacting said catalyst with toluene and hydrogen under toluene disproportionation conditions.

13. A method according to claim 9, wherein siliceous material is deposited on said catalyst by contacting said catalyst with toluene, hydrogen and an organosilicon compound under toluene disproportionation conditions.

14. A method according to claim 9, wherein siliceous material is deposited on said catalyst by the steps of:
   (a) combining a bound form of ZSM-5 with an organosilicon compound; and
   (b) calcining the organosilicon containing material in an oxygen containing atmosphere under conditions sufficient to remove organic material therefrom and leave said siliceous material on the bound ZSM-5.

15. A method according to claim 14, wherein steps (a) and (b) are repeated at least once.

16. A process for disproportionating toluene, said process comprising contacting a feedstock with a selectivated catalyst under sufficient disproportionation conditions, said feedstock comprising toluene and hydrogen, wherein said selectivated catalyst comprises ZSM-5, rhenium impregnated onto the catalyst in an amount of at least about 0.01 wt %, and at least one selectivating agent selected from the group consisting of coke and a siliceous material, and wherein the catalyst is selectivated so as to provide at least about 70.7% disproportionation selectivity to para-xylene over other xylene isomers, and further wherein when said selectivating agent is coke, said coke is present in the catalyst in the amount of at least about 2 wt %, and when said selectivating agent is a siliceous material, said siliceous material is present in an amount of at least about 1 wt %.

* * * * *